(12) United States Patent
Schröder et al.

(10) Patent No.: US 10,611,704 B2
(45) Date of Patent: *Apr. 7, 2020

(54) PROCESS FOR THE CYCLOPROPANATION OF OLEFINS USING N-METHYL-N-NITROSO COMPOUNDS

(71) Applicant: Givaudan, S.A., Vernier (CH)

(72) Inventors: Fridtjof Schröder, Hettlingen (CH); Marcel Steck, Schwerzenbach (CH)

(73) Assignee: Givaudan, S.A., Vernier (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/758,795

(22) PCT Filed: Sep. 14, 2016

(86) PCT No.: PCT/EP2016/071630
§ 371 (c)(1),
(2) Date: Mar. 9, 2018

(87) PCT Pub. No.: WO2017/046122
PCT Pub. Date: Mar. 23, 2017

(65) Prior Publication Data
US 2019/0055172 A1    Feb. 21, 2019

(30) Foreign Application Priority Data

Sep. 16, 2015 (GB) .................................. 1516396.7

(51) Int. Cl.
*C07C 2/86* (2006.01)
*C07C 241/00* (2006.01)
*C07C 13/04* (2006.01)
*C07C 243/06* (2006.01)

(52) U.S. Cl.
CPC .............. *C07C 2/86* (2013.01); *C07C 241/00* (2013.01); *C07C 13/04* (2013.01); *C07C 243/06* (2013.01); *C07C 2601/02* (2017.05)

(58) Field of Classification Search
None
See application file for complete search history.

(56) References Cited

U.S. PATENT DOCUMENTS

| | | | | |
|---|---|---|---|---|
| 2,960,536 | A * | 11/1960 | Getz | ........................ C07C 47/21 564/113 |
| 4,650,881 | A | 3/1987 | Larock et al. | |
| 5,854,405 | A * | 12/1998 | Archibald | .............. C07C 245/16 534/565 |
| 6,962,983 | B2 | 11/2005 | Warr et al. | |
| 9,073,924 | B2 | 7/2015 | Burgess et al. | |
| 9,593,073 | B2 | 3/2017 | Proctor | |
| 9,718,741 | B2 * | 8/2017 | Schroeder | .............. C07C 67/347 |
| 2002/0188112 | A1 | 12/2002 | Warr et al. | |
| 2005/0042255 | A1 | 2/2005 | Goeke | |
| 2012/0135477 | A1 | 5/2012 | Breuer et al. | |
| 2013/0273619 | A1 | 10/2013 | Bonnekessel et al. | |
| 2015/0038687 | A1 | 2/2015 | Proctor | |
| 2016/0280615 | A1 | 9/2016 | Schroeder et al. | |

FOREIGN PATENT DOCUMENTS

| | | |
|---|---|---|
| DE | 855 551 | 11/1952 |
| EP | 1 269 982 A1 | 1/2003 |
| WO | WO 01/47869 A1 | 7/2001 |
| WO | WO 2010/131147 A1 | 11/2010 |
| WO | WO 2013/110932 A1 | 8/2013 |
| WO | WO 2015/059290 A1 | 4/2015 |

OTHER PUBLICATIONS

Loebbecke et al. Microreactors for Processing of Hazardous and Explosible Reactions. IChemE Symposium Series No. 153, 2007 (Year: 2007).*
Redemann et al. Diazomethane. Organic Syntheses, Collection vol. 3, p. 244 (1955), vol. 25, p. 28 (1945) (Year: 1955).*
Dzhemilev, U.M., Dokichev, V.A., Sultanov, S.Z. et al. Reactions of Diazoalkanes with Unsaturated compounds 6. Catalytic Cyclopropanation of Unsaturated Hydrocarbons and their Derivatives with Diazomethane. Russian Chemical Bulletin (1989) 38: 1707-1714. (Year: 1989).*
Sen et al. Squalene Analogues Containing Isopropylidene Mimica as Potential Inhibitors of Pig Liver Squalene Epoxidase and Oxidosqalene Cyclase. J Med Chem 1989, 32, 2152-2158 (Year: 1989).*
PCT/EP2016/071630—International Search Report, dated Dec. 7, 2016.
PCT/EP2016/071630—International Written Opinion, dated Dec. 7, 2016.
Great Britain—Search Report, GB1516396.7, dated Jun. 24, 2016.
Donald W. Adamson, et al., "Improved Preparations of Aliphatic Diazo-Compounds, and Certain of Their Properties", Journal of Chemical Sciences, Jan. 1, 1937, pp. 1551-1556.
Arndt, F., "Nitrosomethylurea", Organic Syntheses, 1943, p. 461, vol. 2; 1953, p. 48, vol. 15.
Creary, et al., "Photochemical Behavior of Cyclopropyl-Substituted Benzophenones and Valerophenones", The Journal of Organic Chemistry, Apr. 1, 2011, pp. 2062-2071, vol. 76, No. 1.
Frater, et al., "Synthesis and Olfactory Properties of (−)-(1R,2S)-Georgywood", Tetrahedron Asymmetry, Dec. 13, 2004, pp. 3967-3972. vol. 15, No. 24, Pergamon Press Ltd, Oxford, GB. Abstract Only.

(Continued)

*Primary Examiner* — Philip Y Louie
*Assistant Examiner* — Alyssa L Cepluch
(74) *Attorney, Agent, or Firm* — Curatolo Sidoti Co., LPA; Salvatore A. Sidoti

(57) ABSTRACT

A process of converting a carbon-carbon double bond on a substrate into a cyclopropane ring, which method comprises the step of treating the substrate with a N-alkyl-N-nitroso compound, a transition metal catalyst and an aqueous base, wherein the N-alkyl-N-nitroso compound is formed by reacting an alkyl amine with an alkali metal nitrite in the presence of a mono-basic or di-basic acid, or a mixture thereof, and wherein the N-alkyl-N-nitroso compound is not distilled before it is mixed with the substrate, catalyst and base.

7 Claims, No Drawings

(56) References Cited

OTHER PUBLICATIONS

Gagnon et al., "Palladium-Catalyzed Cross-Coupling Reaction of Tricyclopropylbismuth with Aryl Halides and Triflates", The Journal of Organic Chemistry, May 1, 2008, pp. 3604-3607, vol. 73, No. 9.
Hahn, et al., "Electrical Effects of Cycloalkyl Groups", Journal of the American Chemical Society, Jun. 19, 1968, pp. 3404-3415, vol. 90, No. 13. First page only.
Jones, et al., "The Cyclopropylidene: Generation and Reactions", Jan. 1, 1963, pp. 2754-2759, vol. 85, No. 18. First page only.
Li, Man-Bo, et al., "Cross-Coupling of Grignard Reagents with Sulfonyl-Activated sp$^3$ Carbon-Nitrogen Bonds", Advance Synthesis & Catalysis, Aug. 10, 2011, pp. 1980-1984, vol. 353, Issue 11-12. Absract Only.
Li, Wei-Dong Z., et al., "A Novel Synthesis of Functionalized Allylsilanes", Organic Letters, Apr. 14, 2004, pp. 1849-1852, vol. 6, No. 11.
Loebecke, S. et al., "Microreactors for Processing of Hazardous and Explosible Reactions", IChemE Symposium Series No. 153, pp. 1-6, Fraunhofer Institute for Chemical Technology ICT, Pfinztal, Germany, 2007.
Mastronardi, F., et al., "Continuous Flow Generation of Reactions of Anhydrous Diazomethan Using a Teflon AF-2400 Tube-In-Tube Reactor", Organic Letters, Oct. 15, 2013, pp. 5590-5593, vol. 15, issue 21. Abstract Only.
Matsuda, T., et al., "Activation of a Cyclobutanone Carbon-Carbon Bond over an Aldehyde Carbon-Hydrogen Bond in the Rhodium-catalyzed Decarbonylation", Chemistry Letters, Jan. 1, 2006, pp. 288-289, vol. 35, No. 3. Abstract Only.
Morandi, B. et al.,"Iron-Catalyzed Cyclopropanation in 6 M KOH with in Situ Generation of Diazomethane", Science, Mar. 23, 2012, pp. 1471-1474, vol. 335, No. 6075.
Murahashi, et al., Quintet Carbenes m-Phenylenbis (Phenylmethylene) and m-Pheylenebis (Methylene), Tetrahedron, Jan. 1, 1972, pp. 1485-1496, vol. 28. Abstract Only.
Nefedov, et al., "Cyclopropanation of Unsaturated Compounds with Diazomethane Generated in situr, A New Efficient and Practical Route to Cyclopropane Derivatives", Mendeleev Commun., Jul. 3, 1991, pp. 13-15 vol. 1, No. 2.
Ohtake, Y., et al., "5a-Carba-β-D-glucopyranose Derivaties as Novel Sodium-Dependent Glucose Cotransporter 2 (SGLT2) Inhibitors for the Treatment of Type 2 Diabetes", Bioorganic & Medicinal Chemistry, Aug. 3, 2011, pp. 5334-5341, vol. 19, No. 18. Abstract Only.
Ornstein, Paul, et al., "2-Substituted (2SR)-2-Amino-2((1SR,2SR)-2-Carboxycycloprop-1-yl) Clycines as Potent and Selectice Antagonists of Group II Metabotropic Glutamate Receptors. 2. Effects of Aromatic Substitution, Pharmacological Characterization, and Bioavailability", Journal of Medicinal Chemistry, Jan. 29, 1998, pp. 358-378, vol. 41, No. 3. Abstract Only.
Peng, Y., et al., "Revisiting the Corey-Chaykovsky Reaction: the Solvent Effect and the Formation of Beta-Hydroxy Methlthioethers", Tetrahedron, Feb. 6, 2006, pp. 1209-1215, vol. 62, No. 6.

Rossi, et al., "Scalable in Situ Diazomethane Generation in Continuous-Flow Reactors", Organic Process Research & Development, 2012, pp. 1146-1149, vol. 16, No. 5. Abstract Only.
Szabo, G., et al., "Chemical and Biological Investigation of Cycloporpyl Containing Diaryl-Pyrazole-3-Carboxamides as Novel and Potent Cannabinoid Type 1 Receptor Antagnists", Journal of Medicinal Chemistry, Jul. 23, 2009, pp. 4329-4337, vol. 52, No. 14.
Tomilov, Y., et al., "The First Example of the Generation and Trapping of Diazospiropentane by Unsaturated Compounds", Mendeleev Commun. 1997, pp. 200-201, vol. 7. Abstract Only.
Yovell, J., et al., "AlC13-Induced Reactions of Vinylcyclopropanes", Taterahedron, Jan. 1, 1978, pp. 993-996, vol. 34, No. 7. Abstract Only.
Mochalov, et al., "New Pathway to the Synthesis of Substituted 4H-3,1-Benzoxazines," Chemistry of Heterocyclic Compounds, vol. 39, No. 6, 2003. Abstract Only.
Kappe, et al., "Continuous Flow Generation and Reactions of Anhydrous Diazomethane Using a Teflon AF-2400 Tube-in-Tube Reactor," Organic Letters, vol. 15, No. 21, pp. 5590-5593, Oct. 15, 2013. Abstract Only.
Stark, et al., "Continuous Production of the Diazomethane Precurson N-Mehtyl-N-nitroso-p-toluenesulfonamide: Bath Optimization and Transfer into a Microreactor Setup," Organic Process Research & Development, vol. 13, No. 5, pp. 1014-1021, Aug. 31, 2009. Abstract Only.
Black, "The Preparation and Reactions of Diazomethane," Aldrichimica Acta, vol. 16, No. 1, 1983.
Woehl et al., "Scalable in Situ Diazomethane Generation in Continuous-Flow Reactors", Organic Process Research & Development, 2012, pp. 1146-1149, vol. 16, No. 5. Abstract Only.
E.C.S. Jones, et al. "The Catalytic Decomposition of Nitro-β-alkylamino-ketones. Part I. A New Method of Preparing Diazomethane and Evidence of the Occurrence of Diazotisation in the Aliphatic Series", Journal of Chemical Sciences, Jan. 1, 1933, pp. 363-368.
C. Ernst Redemann, et al., "Diazomethane", Organic Syntheses Collective vol. 3, 1955, pp. 244-247.
Tomilov, et al., "The Interaction of diazoalkanes with unsaturated compounds", Izvestiya Akademii Nayk SSSR Seriya Khimicvheskaya, Issue No. 3, pp. 582-588 (Year: 1984).
Larock, et al., "Palladium-catalyzed annulation of vinylic cyclopropanes and cyclobutanes" Tetrahedron, Feb. 19, 1996, vol. 52, No. 8, pp. 27 43-2758.
Arndt, et al., "Diels-Alder Reactions for the Construction of Cyclopropylarenes" European Journal of Organic Chemistry, Apr. 17, 2012, vol. 2012, No. 16, pp. 3112-3121.
Shi, et al, "Gold(I)- and Brønsted Acid-Catalyzed Ring-Opening of Unactivated Vinylcyclopropanes with Sulfonamides", Advanced Synthesis & Catalysis, vol. 349, No. 10, Jul. 2, 2007, pp. 1619-1623, Wiley-VCH Verlage GmbH & Co.
Virender, et al., "Indium-mediated, highly efficient cyclopropanation of olefins using CH212 as methylene transfer reagent", Tetrahedron Letters 46, 37-38, Year: 2005.
White, et al., "Basic Energy Sciences Advisory Committee Subpanel Workshop Report", Opportunities for Catalysis in the 21st Century, 2002, pp. 1-47. Year: 2002.

\* cited by examiner

PROCESS FOR THE CYCLOPROPANATION OF OLEFINS USING N-METHYL-N-NITROSO COMPOUNDS

CROSS REFERENCE TO RELATED APPLICATIONS

This application is a national stage application of International Application No. PCT/EP2016/071630, filed 14 Sep. 2016, which claims priority from Great Britain Patent Application No. 1516396.7, filed 16 Sep. 2015, which applications are incorporated herein by reference.

FIELD OF THE INVENTION

This disclosure relates to a method of cyclopropanating alkenes.

BACKGROUND TO THE INVENTION

The conversion of a carbon-carbon double bond to a cyclopropane ring is a chemical transformation used commonly in the synthesis of organic chemical compounds. Cyclopropanation on a laboratory scale is commonly performed with the aid of a diazo compound, for example, diazomethane (DAM), and transition metal catalyst typically comprising a copper or palladium complex. Diazo compounds such as DAM are prepared from an N-alkyl-N-nitroso compound, more particularly a N-methyl-N-nitroso compound (MNC), and still more particularly with an MNC having the general formula R(N(NO)Me)x. In order to make such a process useful in industry, it would be highly desirable if both the MNC and the DAM could be formed in-situ, and further reacted without isolation, in order to avoid the hazards associated with handling these toxic materials. Such a process is described in WO 2015059290, wherein an N-alkyl-N-nitroso compound is generated in a liquid phase from a mixture of an amine HNRR', water, $NaNO_2$ and an acid. An organic solvent can be added to the N-alkyl-N-nitroso compound once it is formed to facilitate phase separation. The N-alkyl-N-nitroso compound partitions into the organic solvent provided for that purpose. A biphasic mixture is formed, and the organic phase can be separated from the aqueous phase in a phase separation step. Thereafter, the organic phase containing the N-alkyl-N-nitroso compound is added to an alkene substrate, without having first to isolate it in pure form. As the N-alkyl-N-nitroso compound is in an organic solvent, it can be cleanly and simply transferred into a reaction vessel containing an alkene substrate.

A particularly suitable N-alkyl-N-nitroso compound is N-nitroso-β-methylaminoisobutyl methyl ketone NMK (sometimes referred to as "Liquizald") which can be prepared from the methylamine mesityloxide adduct through nitrosation in the presence of an acid.

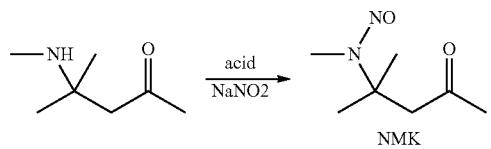

NMK was first prepared by E. C. S. Jones and J. Kenner (JCS 363, 1933) and used for the preparation of diazomethane in the presence of base. Nitrosation (with 2 mol eq $NaNO_2$) was carried out in the presence of HCl (>1 mol eq) and NMK was distilled after extraction from the organic phase. Decomposition of NMK in the presence of base gave DAM which was distilled before being used for the methylenation of benzoic acid.

NMK was also prepared by nitrosation of the methylamine mesityloxide adduct by using 2.5 mol-eq acetic acid and $NaNO_2$ (2.35 mol-eq) in aqueous phase. Treatment of the crude NMK with base gave DAM, which was, once again, distilled before being used for the methylation of an acid (D. W. Adamson, J. Kenner JCS 1553 (1937).

The same method was later on used by C. E. Redemann, F. O. Rice, R. Roberts and H. P. Ward (Org. Synth. Coll. Vol. 3, 244, 1955) employing less acetic acid (HOAc) (1.7 mol-eq) and $NaNO_2$ (1.2 mol-eq) per mol mesityl oxide for the preparation of NMK. The crude NMK was treated with base and DAM was distilled. References for further derivatization of DAM were given, however, the transition metal catalyzed methylenation of double bonds with DAM was unknown at that time.

From these prior art references one can conclude that although NMK and DAM can be efficiently generated from the methylamine mesityloxide adduct by nitrosation in the presence of acetic acid, the NMK and/or DAM were purified and isolated by distillation before being used in any subsequent reactions. Indeed, distillation was deemed necessary to separate NMK and/or DAM from acetic acid as methylation of acetic acid would occur as soon as DAM is generated. In other words, acetic acid is a competitive substrate in any methylation reaction and would thus decrease the yield of any desired methylenated product. The reaction of DAM with acetic acid is well documented in the art, see for example WO 0147869.

The transition metal catalyzed methylenation of alkenes with diazomethane formed from NMK has been described in WO 2013110932. In this reference, NMK is formed by the nitrosation of methylamine mesityl oxide adduct, in the presence of a tribasic acid, notably $H_3PO_4$. The tribasic acid is compared favourably over acetic acid because it reduces or even eliminates acid contamination in the NMK. After phase separation of the organic NMK phase, this procedure produces a 60-80% aqueous $H_3PO_4$ waste solution, and it is emphasized that phase separation is improved by the fact that sodium phosphate salts produced as a by-product of the reaction are close to saturation in the aqueous phase, and that the high level of salt saturation reduces the solubility of NMK in the aqueous phase, ensuring high yields and clean separation of NMK. It is emphasized that the use of the tribasic acid results in a cheaper process and a cleaner (less acidified) product than could be produced using prior art methods. In fact, comparative experiments in WO 2013110932 show that whereas the yields of NMK are similar whether one uses the tribasic acid $H_3PO_4$ or the mono-basic acetic acid, in the latter case the NMK product is contaminated by significant amounts of HOAc (6.4% w/w), which would indicate that using the NMK to subsequently generate DAM in order to methylate a substrate would not be appropriate without first purifying the NMK by distillation.

The use of the method described in WO 2013110932, e.g. preparation of NMK using acidification with $H_3PO_4$, to generate diazomethane for the $Pd(OAc)_2$-catalyzed cyclopropanation of a 1,1-disubstituted alkene has been described by Markus Baenziger (31st International Conference, Organic Process Research and Development, Sep. 29-Oct. 1, 2014, Cologne, Germany).

WO 2015059290 discloses an efficient Pd(acac)$_2$-catalyzed cyclopropanation of a terminally mono-substituted alkene producing diazomethane directly (without nitrogen sparging) in a biphasic reaction mixture consisting of catalyst, substrate, aqueous base and NMK. As stated in Example 7, NMK was prepared as described in WO 2013110932, using H$_3$PO$_4$ for acidification.

When investigating this route for the purpose of assessing its potential as an industrially scalable process, applicant found however, that generating NMK (and by extension, any N-alkyl-N-nitroso compound) using a tribasic acid such as H3PO4, decomposing it to form DAM in-situ without purification or isolation of either NMK or DAM, and reacting the DAM with an alkene substrate to cyclopropanate that substrate, resulted in a poorly reproducible reaction.

Applicant believes—without intending to be bound by any particular theory—the poor reproducibility may have as its cause, the generation of high levels of nitrous gases during NMK formation, which could contaminate both the NMK and the DAM, and poison the catalyst used in the cyclopropanation step.

In addition to this empirical observation, the relatively high price of H$_3$PO$_4$, sustainability issues related to future supply of limited phosphorus resources, and generation of phosphorus waste from the reaction, particularly when using stoichiometric amounts of H$_3$PO$_4$, led the applicant to conclude that the use of a tri-basic acid and in particular H$_3$PO$_4$, contrary to suggestions in the prior art, was not a viable, industrially scalable route.

There remains a need to address the deficiencies in the prior art and to provide a method of cyclopropanating alkene functionality on a substrate that is safe, cost effective, and can reliably produce industrial quantities of product in high yields.

SUMMARY OF THE INVENTION

The disclosure provides in a first aspect a method of converting a carbon-carbon double bond on a substrate into a cyclopropane ring, which method comprises the step of treating the substrate with a N-alkyl-N-nitroso compound, a transition metal catalyst and an aqueous base, wherein the N-alkyl-N-nitroso compound is formed by reacting an alkyl amine and NaNO$_2$ in the presence of a mono-basic or di-basic acid or mixtures of said acids, more particularly a mono-basic carboxylic acid such as acetic acid or a di-basic inorganic acid such as sulfuric acid, and wherein the N-alkyl-N-nitroso compound is not distilled before it is mixed with the substrate, catalyst and base for the purpose of cyclopropanation in this mixture.

DETAILED DESCRIPTION OF THE INVENTION

Although the preparation of a N-alkyl-N-nitroso compound, and its subsequent use, without purification or isolation, in the conversion of a carbon-carbon double bond to a cyclopropane ring is known in the art, there is a clear prejudice in the art to do this if the acid employed in the preparation of the N-alkyl-N-nitroso compound is an acid which can be methylated, such as a mono basic carboxylic acid and more particularly acetic acid.

The applicant was surprised to find, therefore, that the cyclopropanation reaction proceeded to produce reliably high yields of cyclopropanated product on an industrial scale. Furthermore, the use of these acids is relatively inexpensive compared with the use of tribasic acids such as H$_3$PO$_4$. Further still, the reaction is advantageous from a sustainability point of view due to the generation and degradation of carboxylic acids in the biosphere.

In exercising the present invention the preferred mono- or di-basic acids are sulphuric acid, or mono- or di-basic carboxylic acids, such as $C_1$-$C_{20}$ carboxylic acids, which may be linear, branched or cyclic, and which may be saturated, or contain saturation, and may or may not be substituted with functional groups. Of course, for reasons related to economy, it is preferred to use low-cost carboxylic acids with low molecular weight such as formic acid, acetic acid or propionic acid, most preferably acetic acid. $C_1$-$C_{20}$ mono-, bis, tri and polyacids are also an option as well as mixtures of carboxylic acids or mixtures of carboxylic acids and inorganic acids such as dibasic sulfuric acid or mixtures of mono- and dibasic inorganic acids.

In a particular embodiment of the invention mixtures of a carboxylic acid, e.g. acetic acid, with stronger (i.e. lower pKa) organic and inorganic acids can be employed in the formation of N-alkyl-N-nitroso compounds. Typical solutions might include 5 to 50% solutions of said stronger acid in said carboxylic acid, and more particularly 5 to 20% is preferred, as higher levels of the stronger acid in the carboxylic acid can be detrimental to phase separation, yield and purity of N-alkyl-N-nitroso compounds, as well as produce high levels of nitrous gases, which as stated above, can poison the catalyst in the subsequent cyclopropanation step. An exception to this appears to be use of H$_2$SO$_4$ as the acidification reagent in the nitrosation reaction. In contrast to other strong acids, such as HCl, HNO$_3$ and methyl sulphonic acid for example, H$_2$SO$_4$ can be used without a carboxylic acid, although it can also be employed 0.1-1.5 eq, more preferably with 0.5-1 eq., in combination with acetic acid.

These findings were all the more surprising given that from the literature, one would predict, substantially reduced yields both of N-alkyl-N-nitroso compound and the final cyclopropanated substrate if mono- or di-basic acids, and in particular acetic acid is employed instead of the favoured tribasic acids, and in particular H$_3$PO$_4$. In fact, applicant found that the yields of cyclopropanated product were comparable irrespective of whether one employs acetic acid or other mono- and dibasic acids in the acidification step or H$_3$PO$_4$. As stated above, although the use of H$_3$PO$_4$ may carry with it certain advantages, the applicant believes that the generation of nitrous gases may play a negative role, and it was observed that lower levels of nitrous gases were formed when using acetic acid compared with the use of H$_3$PO$_4$. In the case of the acidification with acetic acid less nitrous gases were generated, based on the observation that the less brownish coloration of the N-alkyl-N-nitroso compound layer and less brown vapors in the nitrogen waste stream, compared with a process wherein acidification was carried out using H$_3$PO$_4$.

Any of the N-alkyl-N-nitroso compounds disclosed in WO 2015059290 may be employed in the present invention. The N-alkyl-N-nitroso compounds may be made in accordance with prior art methods, in which an alkyl amine, alkyl amide, alkyl urethane or alkyl urea HNRR' is reacted with an acid and an alkali metal nitrite, such as NaNO$_2$. The alkyl amine may be commercially available material, or it may be formed by reacting an aliphatic amine H$_2$NR with a suitable starting material reactive with the aliphatic amine, such as an α,β-unsaturated ketone. Preparative methods are set out in WO 2015059290. A particularly preferred N-alkyl-N-nitroso compound is N-nitroso-β-methylaminoisobutyl methyl ketone (NMK). This particular material may be prepared when methylamine is reacted with the α,β-unsaturated ketone—mesityl oxide—to form a methylamine mesityl oxide adduct (corresponding to HNRR', above). The adduct can then be further reacted with NaNO₂ and an acid to provide NMK. Methods of forming NMK are described in WO2013110932, which is hereby incorporated by reference.

The reaction to produce the N-alkyl-N-nitroso compounds may be carried out in a biphasic mixture. Before, during, or after the reaction is completed, one can add an organic solvent, which is a solvent for the alkyl-N-nitroso compound, and the organic layer, containing the crude N-alkyl-N-nitroso compound can be separated and used in the subsequent cyclopropanation reaction without further purification, for example by distillation. Optionally, however, the organic layer containing the N-alkyl-N-nitroso compound may be washed with an aqueous washing procedure known in the art, for example washing with a salt solution, provided no further acidification takes place or any basification does not increase the pH above a level of moderate basicity, e.g. 7 to 8.5, to prevent liberation of diazomethane. Such a washing procedure ideally removes nitrous gases, traces of acid, e.g. acetic acid, and other impurities. In a further optional procedure, one may subject the organic layer to a degassing procedure using inert gas (e.g. nitrogen) to remove any traces of nitrous gases.

The cyclopropanation reaction is carried out in a biphasic mixture, in which the organic phase is a solvent for the N-alkyl-N-nitroso compound. Suitable solvents include ethers and toluene, and more particularly tetrahydrofuran, dimethoxyethane, dioxane and dimethylisosorbide. In a first step, the organic phase containing the N-alkyl-N-nitroso compound is added to a mixture containing the substrate to be converted, aqueous base and catalyst. The aqueous base decomposes the N-alkyl-N-nitroso compound to form the diazoalkane, which in the presence of the catalyst converts the carbon-carbon double bond into a cyclopropyl group. Upon completion of the cyclopropanation reaction, the mixture is phase separated and the organic phase, containing the target cyclopropanated compound is obtained.

The methods herein described may be carried out under flow conditions in a flow reactor. Methods and apparatus for carrying out flow chemistry are well known in the art and do not require further elaboration here.

Details of the cyclopropanation process, as well as the reagents, solvents and reaction conditions and work-up conditions employed are set forth in WO 2015059290, which is hereby incorporated by reference for this purpose.

Catalysts useful in the present invention are transition metal catalysts, more particularly palladium catalysts, still more particularly the palladium catalysts, Pd(acac)₂, Pd(OAc)₂ or PdCl₂.

Any double bond-containing substrate may be converted in accordance with the method of the present invention, to form all manner of useful and desirable cyclopropanated target compounds. Suitable double bond-containing substrates and the target cyclopropanated compounds, especially useful in fragrance, cosmetic and flavour applications are set forth and described in WO 2015059290, which is hereby incorporated by reference for this purpose.

Particular substrates include terminal (i.e. mono-substituted) alkenes. More particularly, compounds according to the general formulae

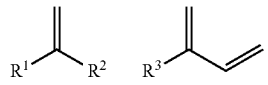

wherein $R^1$ and $R^2$ may, independently, represent H, alkyl, alkylidene, or aryl, which be branched or unbranched and substituted or unsubstituted; and $R^3$ may be an alkyl, alkylidene, or aryl, which may be branched or unbranched and substituted or unsubstituted.

Still more particularly, the substrate may be an isoprenoid, such as alpha or beta farnesene.

Target compounds that may be formed by a method according to the present invention include compounds of the formula

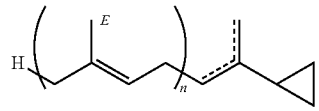

in which n=0, 1, 2 or 3.

In a particular embodiment the target compound is

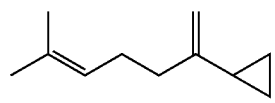

In another particular embodiment the target compound is

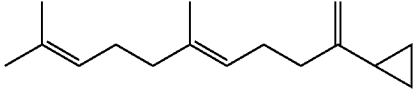 [SMILES: C=C(CC/C=C(\C)CCC=C(C)C)C1CC1]

Target compounds according to the present invention are useful precursors to compounds that are useful ingredients in perfumery.

There now follows a series of examples serving to further illustrate the invention.

EXAMPLES

¹H-NMR: The reported NMR spectra were measured in CDCl₃ at 400 MHz if not stated otherwise. The chemical shifts are reported in ppm downfield from TMS. The quantification of Liquizald was performed using an internal standard (anisaldehyde) with known purity ty in d₆-DMSO. Additionally, to guarantee full relaxation of the signals, the relaxation time d1 was set to 56 s.

Example 1

Preparation of (N-methyl-N-nitroso)-4-amino-4-methyl-2-pentanone (NMK) by Nitrosation in the Presence of Carboxylic Acids

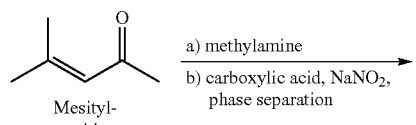

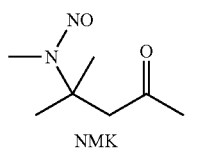

NMK

Mesityl oxide (10 g, 0.1 mol) is added dropwise over 15 min to methylamine (40% in water, 8.3 g, 0.11 mol) at 5-15° C. under external cooling and stirring. The resulting orange solution is stirred for one hour at room temperature and cooled to 10° C. where formic acid (98%, 8.4 g, 0.18 mol) is added dropwise over 15 min at 10-20° C. Then a 30% solution of sodium nitrite (8.85 g, 0.125 mol) in water (21 g) is added dropwise over 10 min at 10-15° C. The biphasic mixture is left under stirring and at room temperature overnight (16 h). After phase separation (1 h) 15.25 g (68% based on mesityl oxide) of an organic layer is obtained consisting mainly of (N-methyl-N-nitroso)-4-amino-4-methyl-2-pentanone (NMK) with a purity of 72% according to $^1$H-NMR with internal standard.

The following table shows results from the variation of this procedure using different carboxylic acids:

Example 2

Preparation of (N-methyl-N-nitroso)-4-amino-4-methyl-2-pentanone (NMK) by Nitrosation in the Presence of Acetic Acid and Stronger Acids

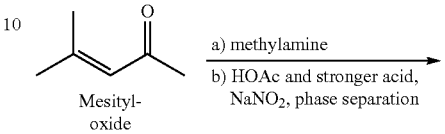

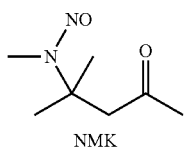

NMK

Mesityl oxide (10 g, 0.1 mol) is added dropwise over 15 min to methylamine (40% in water, 8.5 g, 0.11 mol) at 5-15° C. under external cooling and stirring. The resulting orange solution is stirred for one hour at room temperature and cooled to 10° C. where acetic acid (100%, 10 g, 0.1 mol) is added added dropwise over 15 min at 10-20° C. Then a 30% solution of sodium nitrite (8.85 g, 0.125 mol) in water (21 g) is added dropwise over 10 min at 10-15° C. The biphasic mixture is left under stiffing and at room temperature overnight (16 h). After phase separation (1 h) 14.25 g (62% based on mesityl oxide) of an organic layer is obtained consisting mainly of (N-methyl-N-nitroso)-4-amino-4-methyl-2-pentanone (NMK) with a purity of 70% according to $^1$H-NMR with internal standard.

The following table shows results from the variation of this procedure using acetic acid in combination with different stronger acids

| run | acid | acid conc | mol-eq acid/ mesityl oxide | formation of NOx gases[b] | purity[a] | yield[c] |
|---|---|---|---|---|---|---|
| comparison | phosphoric | 75% in $H_2O$ | 0.9 | insignificant | 77% | 73% |
| 1 | formic | pure | 1.75 | weak | 72% | 68% |
| 2 | acetic | pure | 1.75 | insignificant | 69% | 66% |
| 3 | acetic | pure | 1.6 | insignificant | 70% | 62% |
| 4 | α-hydroxy-isobutyric | 75% in $H_2O$ | 1.75 | middle | 59% | 38% |
| 5 | lactic | pure | 1.75 | insignificant | 71% | 62% |
| 6 | glyolic | pure | 1.75 | insignificant | 74% | 61% |

Conditions: Addition of carboxylic acids to the methyl amine/mesityl adduct followed by $NaNO_2$ addition and phase separation as described above.
[a] determination of the purity by $^1$H-NMR with internal standard anisaldehyde.
[b] brown coloration of reaction mixture, brown vapors over reaction surface and in the exhaust tube.
[c] based on quantity of organic phase and purity.

| run | HOAc and stronger acid | mol-eq HOAc[c] | mol-eq stronger acid[c] | formation of NOx gases[b] | purity[a] | yield[e] |
|---|---|---|---|---|---|---|
| comparison | ./. | 1.6 | ./. | insignificant | 70% | 62% |
| 1 | 65% HNO$_3$ | 1.8 | 0.1 | insignificant | 69% | 64% |
| 2 | 65% HNO$_3$ | 1.3 | 0.3 | insignificant | 76% | 66% |
| 3 | 65% HNO$_3$ | 0.5 | 0.8 | intermediate | much less organic phase | |
| 4 | 65% HNO$_3$ | ./. | 1.75 | significant | much less organic phase | |
| 5 | 32% HCl | 1.6 | 0.1 | insignificant | 72% | 68% |
| 6 | 32% HCl | 1.3 | 0.3 | insignificant | 74% | 68% |
| 7 | 32% HCl | 0.5 | 0.8 | intermediate | much less organic phase | |
| 8 | 32% HCl | ./. | 1 | significant | 63% | 32% |
|  | 32% HCl | ./. | 1 + 1[d] | intermediate | 61% | 39% |
| 9 | 98% H$_2$SO$_4$ | 1.6 | 0.1 | insignificant | 69% | 64% |
| 10 | 98% H$_2$SO$_4$ | 1.3 | 0.3 | intermediate | 65% | 71% |
| 11[c] | 80% H$_2$SO$_4$ | ./. | 0.65 | insignificant | 63% | 58% |
| 12[d] | 80% H$_2$SO$_4$ | ./. | 1 | intermediate | 69% | 50% |
| 13 | 80% H$_2$SO$_4$ | ./. | 2 | significant | no phase separation | |
| 14 | CF$_3$SO$_3$H | 1 | 0.1 | insignificant | 66% | 65% |
| 15 | 75% MeSO$_3$H | 1 | 0.1 | insignificant | 71% | 68% |
| 16 | 75% MeSO$_3$H | ./. | 1.75 | significant | much less organic phase | |

Conditions: Addition of pure acetic acid (and stronger acid) to the methyl amine/mesityl adduct followed by NaNO$_2$ addition and phase separation as described above.
[a]Determination of the purity by $^1$H-NMR with internal standard anisaldehyde.
[b]brown coloration of reaction mixture, brown vapors over reaction surface and in the exhaust tube.
[c]stronger acid dissolved in acetic acid.
[d]method described in *JCS* 363, 1933.
[e]based on quantity of organic phase and purity.

Example 3

Diazomethane cyclopropanation with (N-methyl-N-nitroso)-4-amino-4-methyl-2-pentanone (NMK) Made Through Nitrosation in the Presence of HOAc

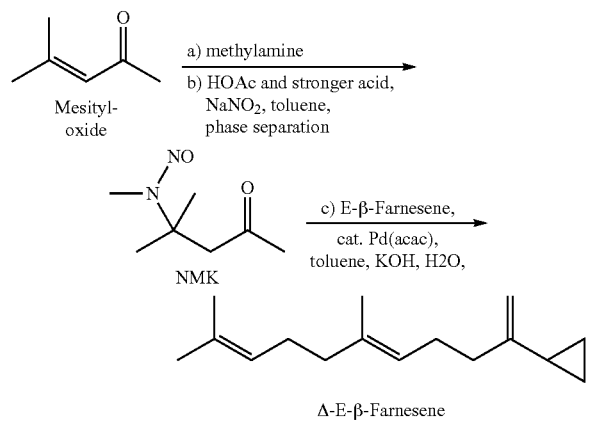

Mesityl oxide (68.8 g, 0.7 mol) is added dropwise over 1 h to methylamine (40% in water, 58.1 g, 0.75 mol) at 5-15° C. under external cooling and stirring. The resulting orange solution is stirred for one hour at room temperature. Water (140 ml) and toluene (70 ml) are added, followed by dropwise addition of acetic acid (100%, 115 g, 1.9 mol) over 1 h at 10-20° C. Then a 30% solution of sodium nitrite (49.8 g, 0.7 mol) in water (116 g) is added dropwise over 60 min at 20-25° C. The biphasic mixture is left under stirring and at room temperature overnight (16 h). After phase separation (1 h) 155.23 g of an organic layer is obtained consisting mainly of (N-methyl-N-nitroso)-4-amino-4-methyl-2-pentanone (NMK) which is flushed with nitrogen through a sintered tube for 1 h which turns the opaque organic phase into a clear solution.

Pd(acac)$_2$ (0.1 g, 0.33 mmol) are added to a solution of E-β-Farnesene 98% (51.5 g, 0.25 mol) in toluene (150 ml), followed by KOH (49.9 g, 0.76 mol) in water (208.5 g) under strong stirring. The (N-methyl-N-nitroso)-4-amino-4-methyl-2-pentanone layer (155.2 g) is added over 2 h at 25° C. GC after 0.5 h shows E-β-Farnesene (4%), Δ-E-β-Farnesene (88%), and Δ$_2$-E-β-Farnesene (8%). After 17 h (same GC profile) the phases are separated. The water phase is washed with toluene (100 ml), the organic phase is washed with water (250 ml), acetic acid (250 g), water (250 ml), 10% NaOH (250 ml) and water (2×250 ml). The combined organic layers are dried over MgSO4, filtered and the solvent is removed under reduced pressure giving 63.6 g of crude Δ-E-β-Farnesene which is purified by flash distillation giving 0.73 g of E-β-Farnesene (0.5%), 48.12 g of Δ-E-β-Farnesene (89%) and 3.1 g Δ$_2$-E-β-Farnesene (5%) whose analytical data are identical to the ones described in WO 2015059290.

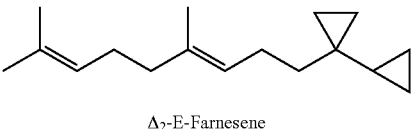

Δ$_2$-E-Farnesene

The following table shows results from the variation of this procedure using different amounts of catalyst and/or dibasic acid H$_2$SO$_4$.

| run | mol-eq$^a$ acid | mol-eq$^a$ NaNO$_2$ | mol %$^a$ Pd(acac)$_2$ | conversion | $\Delta_1$ | $\Delta_2$ | isolated yield$^b$ |
|---|---|---|---|---|---|---|---|
| comparison | 2.8 H$_3$PO$_4$ | 2 | 0.13% | 100% | 91% | 8% | 86% |
| 1 | 7.6 HOAc | 2.8 | 0.13% | 96% | 88% | 8% | 87% |
| 2 | 7.6 HOAc | 2.8 | 0.05% | 81% | 76% | 3% | n.d. |
| 3 | 7.6 HOAc | 2.8 | 0.02% | 67% | 57% | 1% | n.d. |
| 4 | 1.5 H$_3$PO$_4$ | 2.1 | 0.02% | 68% | 53% | 2% | n.d. |
| 5 | 1.75 H$_2$SO$_4$ | 2.8 | 0.02% | 52% | 40% | ./. | n.d. |
| 6 | 1.75 H$_2$SO$_4$ | 3 | 0.13% | 100% | 90% | 10% | 87% |

Conditions: Cyclopropanation at 25° C.
$^a$mol-eq or mol % based on farnesene.
$^b$After short-path distillation and corrected by purity of E-$\Delta_1$-Farnesene.
n.d. = not determined.

The invention claimed is:

1. A method for forming a compound of the formula

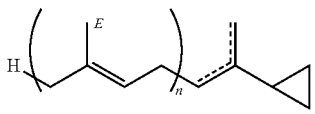

in which n=1, 2, or 3, the method comprising
   forming a N-alykl-N-nitroso compound by reacting an alkyl amine with an alkali metal nitrite in the presence of an acid comprising a mono-basic or di-basic carboxylic acid, or a mixture thereof,
   converting a carbon-carbon double bond on a substrate into a cyclopropane ring by mixing the substrate with the N-alykl-N-nitroso compound, a palladium catalyst, and an aqueous base, thereby forming the compound of the formula above,
   wherein the N-alkyl-N-nitroso compound is not distilled before it is mixed with the substrate, the palladium catalyst, and the aqueous base.

2. The method according to claim 1, wherein the acid is formic acid or acetic acid.

3. The method according to claim 1, wherein the acid is a mixture of the mono-basic or di-basic carboxylic acid and an organic or inorganic acid having a lower pKa than said carboxylic acid.

4. The method according to claim 3, wherein the acid is a mixture of acetic acid and sulphuric acid.

5. The method according to claim 1, wherein the N-alkyl-N-nitroso compound is (N-methyl-N-nitroso)-4-amino-4-methyl-2-pentanone.

6. The method according to claim 1, wherein the compound formed has the following structure

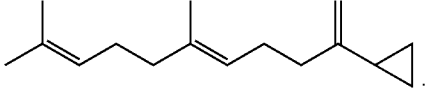 [SMILES: C=C(CC/C=C(\C)CCC=C(C)C)C1CC1]

7. The method according to claim 1, wherein the palladium catalyst is Pd(acac)$_2$, Pd(OAc)$_2$ or PdCl$_2$.

* * * * *